(12) United States Patent
Kown

(10) Patent No.: US 6,453,799 B1
(45) Date of Patent: Sep. 24, 2002

(54) AUTOMATIC VENDING MACHINE WITH FUNCTIONAL WATER GENERATOR

(75) Inventor: Dong Heon Kown, Seoul (KR)

(73) Assignee: EcoAid Corp., Seoul (KR)

( * ) Notice: Subject to any disclaimer, the term of this patent is extended or adjusted under 35 U.S.C. 154(b) by 0 days.

(21) Appl. No.: 09/740,674

(22) Filed: Dec. 18, 2000

(30) Foreign Application Priority Data

Nov. 14, 2000 (KR) ........................................ 2000-67358

(51) Int. Cl.[7] .............................. A47J 31/00; C02F 1/30
(52) U.S. Cl. ........................ 99/286; 99/290; 210/243; 210/748; 422/186.12
(58) Field of Search .............................. 99/286, 239 R, 99/290, 280, 281, 282, 283; 210/243, 748; 422/186.07, 186.12

(56) References Cited

U.S. PATENT DOCUMENTS

| | | | | |
|---|---|---|---|---|
| 4,649,809 A | * | 3/1987 | Kanezashi | 99/290 |
| 5,113,751 A | * | 5/1992 | Holcomb et al. | 99/286 |
| 5,944,973 A | * | 8/1999 | Hall | 99/286 X |
| 5,976,363 A | * | 11/1999 | Monroe et al. | 99/357 X |

* cited by examiner

Primary Examiner—Reginald L. Alexander
(74) Attorney, Agent, or Firm—Perkins Coie LLP

(57) ABSTRACT

Provided is a cup-beverage automatic vending machine which can supply beverages in a sanitary manner by additionally installing an apparatus for generating functional water such as ozone water or electrolyzed water in a high concentration to a conventional automatic vending machine. The automatic vending machine includes a water supplier for supplying drinking water, a plurality of ingredient containers for storing beverage ingredients, a mixing tub for mixing the drinking water supplied from the water supplier and the beverage ingredients supplied from the ingredient containers, a discharge duct through which the mixed beverage is discharged, and a functional water generator for generating functional water in the water supplier by facing electrodes provided to operate in water. According to the automatic vending machine, the functional water such as ozone water or electrolyzed water is generated in the drinking water stored in the water tank or in the water supply duct, and simultaneously sterilize, disinfect, deodorize and wash the drinking water as well as the containers and conduits installed in the machine, thereby achieving a sanitary automatic vending machine.

17 Claims, 12 Drawing Sheets

AUTOMATIC VENDING MACHINE WITH FUNCTIONAL WATER GENERATOR

BACKGROUND OF THE INVENTION

1. Field of the Invention

The present invention relates to an automatic vending machine for drinks, and more particularly, to a cup-beverage automatic vending machine which can supply beverages in a sanitary manner by additionally installing an apparatus for generating functional water such as ozone water or electrolyzed water in a high concentration to a conventional automatic vending machine.

2. Description of the Related Art

In general, an automatic vending machine for drinks, in particular, a cup-beverage automatic vending machine is configured such that when a user puts a coin into a coin slot and selects one kind of a beverage, water stored in a water tank is heated or cooled, if necessary, and then mixed with beverage ingredients, and the mixed beverage is poured into a cup, after then the user takes out the cup filled with the beverage. The greatest concern in such an automatic vending machine is sanitation. In particular, the water stored in the water tank is easily contaminated, resulting in serious deterioration. Also, the water leaking out when poured into a cup must be often withdrawn. To solve the sanitation problem of the automatic vending machine of a cup-beverage type, there have been conventionally proposed an automatic vending machine configured to sterilize or purify water by installing a sterilizer using a filter, a UV lamp or an ozone generator.

For example, Korean Patent Laid-open Publication No. 1999-18983 describes an automatic vending machine adopting a method of sterilizing drinking. water supplied from a water tank using a UV lamp, which is shown in FIG. 1. Referring to FIG. 1, a water supply device for supplying water and a beverage ingredient supply device for storing and supplying beverage ingredients are installed in a casing. In detail, the water supply device includes a water supply tank 51 for storing a drinking water, a hot water tank 53 for heating the water supplied from the water supply tank 51, and a guide duct 56 for guiding the water supplied from the water supply tank 51 to the hot water tank 53. The ingredient supply device includes a plurality of ingredient storage tanks 55 in front of the hot water tank 53, and a mixing tub 54 and an outlet duct 57 under the storage tanks 55. The ingredients supplied from the storage tanks 55 and the hot water supplied from the hot water tank 53 are mixed in the mixing tub 54 and then the mixed beverage is discharged outside via the outlet duct 57 by a supply cock 58. Here, a UV lamp 52, which is a sterilizer, installed at a predetermined area of the guide duct 56, is provided to sterilize the water passing through the guide duct 56.

However, in the automatic vending machine using a UV lamp, a sufficient sterilizing efficiency cannot be attained. Also, such contamination as developed after radiating by the UV lamp is unavoidable.

Korean Utility Model Laid-open Publication No. 1993-26298 discloses an automatic vending machine having an ozone generator. FIGS. 2a and 2b show a conventional automatic vending machine adopting a method in which the water in a water tank is sterilized with ozone generated in the air by means of an ozone generator. Referring to FIG. 2b, a distribution plate 64 is installed in the lower portion of a water supply tank 61 which is connected with a water supply duct 65 and a water refill duct 66, and an ozone generator 62 for generating ozone in the air is connected to a supply conduit 63 in one side of the distribution plate 64. The ozone gas generated in the air by the ozone generator 62 is supplied to the distribution plate 64 to sterilize the water in the water supply tank 61.

However, an ozone gas requires a considerable time to be dissolved in water, and the time is dependent upon the shape and size of the ozone gas when it is brought into contact with water. In particular, ozone gas particles with small size are advantageously dissolved in water. Thus, in the automatic vending machine based on a method in which ozone gas is generated in the air and then dissolved in water, a separate device is required for making ozone gas into fine particles. Further, the undissolved ozone gas emanated into the air would be harmful to the user. Thus, it is necessary to remove the harmful ozone gas using a separate device, which increases financial burden of equipment. Also, the user's safety cannot be ensured due to the emanated ozone gas.

Alternatively, the water in the automatic vending machine may be sterilized using chemicals such as chlorine ($Cl_2$) gas. In this case, however, trihalomethane (THM), which causes environmental pollution and is a carcinogen, may be produced.

In addition to the sanitation problem of the water stored in a water tank, the water leaking outside when poured into a cup after the drinking water and beverage materials are mixed, unless being often withdrawn or disposed of, may infect the machine to cause another sanitation problem.

SUMMARY OF THE INVENTION

To solve a sanitation problem encountered in the conventional automatic vending machine and to solve safety and equipment problems encountered in the conventional automatic vending machine with an ozone generator, it is an object of the present invention to provide a sanitary automatic vending machine which can simultaneously and safely perform sterilization, disinfection, deodorization and washing of water and beverages as well as containers and conduits installed inside the machine, by additionally installing a simple apparatus for generating functional water including ozone water by means of electrodes operating in water in a cup-beverage automatic vending machine.

The present invention further provides a washing method of an automatic vending machine and a water supplying method therein.

To accomplish the above object of the present invention, there is provided an automatic vending machine including a water supplier for supplying drinking water, a plurality of ingredient containers for storing beverage ingredients, a mixing tub for mixing the drinking water supplied from the water supplier and the beverage ingredients supplied from the ingredient containers, a discharge duct through which the mixed beverage is discharged, and a functional water generator for generating functional water in the water supplier by facing electrodes provided to operate in water.

Here, the automatic vending machine may further include a cold/hot water tank for cooling or heating the drinking water supplied from the water supplier, and a recycling duct for recycling a liquid leaked from the discharge duct into the water supplier. The recycling duct may include a purifying filter and another functional water generator.

In the present invention, the functional water generator may be an ozone water generator having at least one pair of facing electrodes or an electrolyzed water generator having at least one pair of facing electrodes disposed with a separating layer interposed therebetween. The facing electrodes are made of platinum (Pt), a platinum/palladium (Pt/Pd) alloy or a Pt group/Pd alloy. Alternatively, the facing electrodes may be made of a conductive metal coated with platinum (Pt), a platinum/palladium (Pt/Pd) alloy or a Pt group/Pd alloy. The conductive metal is preferably titanium (Ti). In the case of using the Pt/Pd alloy, 85.0 to 99.95 wt % of Pt and 15.0 to 0.05 wt % of Pd are preferably contained in the alloy. Also, the facing electrodes are preferably carbon electrodes having electric conductivity.

The facing electrodes may be of a plane type, a flat panel type having one or more holes, a small strip type, a fine wire type, a fish bone type, a mesh type or a cylinder type, and the distance of the facing electrodes is preferably in the range of 0.1 to 1 mm.

Also, the automatic vending machine may further include a power source for applying a voltage to the functional water generator. The power may be a direct-current (DC) voltage, a pulse voltage, a square wave pulse voltage, a sequence-controlled pulse voltage or an alternating pulse voltage.

The automatic vending machine may further include a power source for applying a voltage to the functional water generator, a sensor for sensing the concentration of the functional water supplied via the functional water generator, and a controller for receiving information of the concentration of the functional water from the sensor and controlling the voltage to be applied to the power source.

According to another aspect of the present invention, there is provided an automatic vending machine including means for supplying drinking water, means for supplying beverage ingredients, means for mixing the supplied drinking water and the beverage ingredients, means for discharging the mixed beverage to the outside, and means for generating functional water in the drinking water by means of facing electrodes provided to operate in water.

Here, the functional water may be ozone water or electrolyzed water. The electrolyzed water may include acid water, alkali water or neutral water.

Also, the automatic vending machine may further include means for cooling or heating the supplied drinking water, and means for recycling a liquid leaked from the discharging means to recycle into the drinking water. The recycling means may include a purifying filter and another functional water generating means.

The automatic vending machine may further include means for sensing the concentration of the functional water supplied via the functional water generating means, and means for controlling the generation of the functional water in accordance with the concentration of the functional water.

According to another aspect of the present invention, there is provided a washing method of an automatic vending machine having a water supplier for supplying drinking water, a plurality of ingredient containers for storing beverage ingredients, a mixing tub for mixing the drinking water supplied from the water supplier and the beverage ingredients supplied from the ingredient containers, and a discharge duct through which the mixed beverage is discharged, wherein the method includes the steps of generating functional water in the water supplier by facing electrodes provided to operate in water, and discharging the functional water to the discharge duct through the mixing tub.

Alternatively, the present invention provides a washing method of an automatic vending machine having a water supplier for supplying drinking water, a plurality of ingredient containers for storing beverage ingredients, a mixing tub for mixing the drinking water supplied from the water supplier and the beverage ingredients supplied from the ingredient containers, a discharge duct through which the mixed beverage is discharged, and a recycling duct for recycling a liquid leaked from the discharge duct into the water supplier, wherein the method includes the steps of generating functional water in the water supplier by facing electrodes provided to operate in water, discharging the functional water to the discharge duct through the mixing tub, recycling the discharged functional water into the water supplier through the recycling duct, and discharging the recycled functional water to the discharge duct through the mixing tub.

The washing method may further include the steps of sensing the concentration of the supplied functional water, and controlling the generation of the functional water in accordance with the concentration of the supplied functional water.

According to another aspect of the present invention, there is provided a method for supplying water to an automatic vending machine having a water supplier for supplying drinking water, a plurality of ingredient containers for storing beverage ingredients, a mixing tub for mixing the drinking water supplied from the water supplier and the beverage ingredients supplied from the ingredient containers, and a discharge duct through which the mixed beverage is discharged, wherein the method includes the steps of generating ozone water in the water supplier by facing electrodes provided to operate in water, mixing the ozone water and the beverage ingredients supplied from the ingredient containers, and discharging the mixed beverage through the discharge duct.

The feature of the present invention lies in that the functional water generator for generating functional water having various functions of sterilization, disinfection, deodorization or washing, is installed in the water supplier, that is, in the water tank or water supply duct of a cup-beverage automatic vending machine, to generate functional water in the water contained in the water tank or passing through the water supply duct, thereby performing sterilization, disinfection, deodorization and washing of water and beverages as well as containers and conduits installed in the machine. In the automatic vending machine according to the present invention, the functional water generator includes at least one pair of facing electrodes so that when a voltage is applied to the electrodes, the water contained in the water tank or passing through the water supply duct is electrolyzed to generate functional water. While the conventional automatic vending machine with an ozone gas generator operated in air requires an equipment for dissolving the generated ozone into the water stored in the water tank, in the automatic vending machine according to the present invention, sterilization, disinfection, deodorization or washing of both containers and ducts in the machine and drinking water can be simultaneously performed without such additional equipment or causing a safety problem due to undissolved ozone gas.

BRIEF DESCRIPTION OF THE DRAWINGS

The above object and advantages of the present invention will become more apparent by describing in detail a preferred embodiment thereof with reference to the attached drawings in which:

FIGS. 9A through 9D illustrate an example of an ozone water generator for use in the automatic vending machine according to the present invention, in which FIG. 9A shows one of two facing electrodes, FIG. 9B shows a spacer for maintaining a gap between the facing electrodes, FIG. 9C shows an electrode fixing frame, and FIG. 9D shows a bare-type ozone water generator;

DESCRIPTION OF THE PREFERRED EMBODIMENTS

The present invention will now be described by the following embodiments in more detail with reference to the accompanying drawings. However, these embodiments are illustrations only provided for a better understanding of the invention, not for the purpose of limiting.

Figure 1:
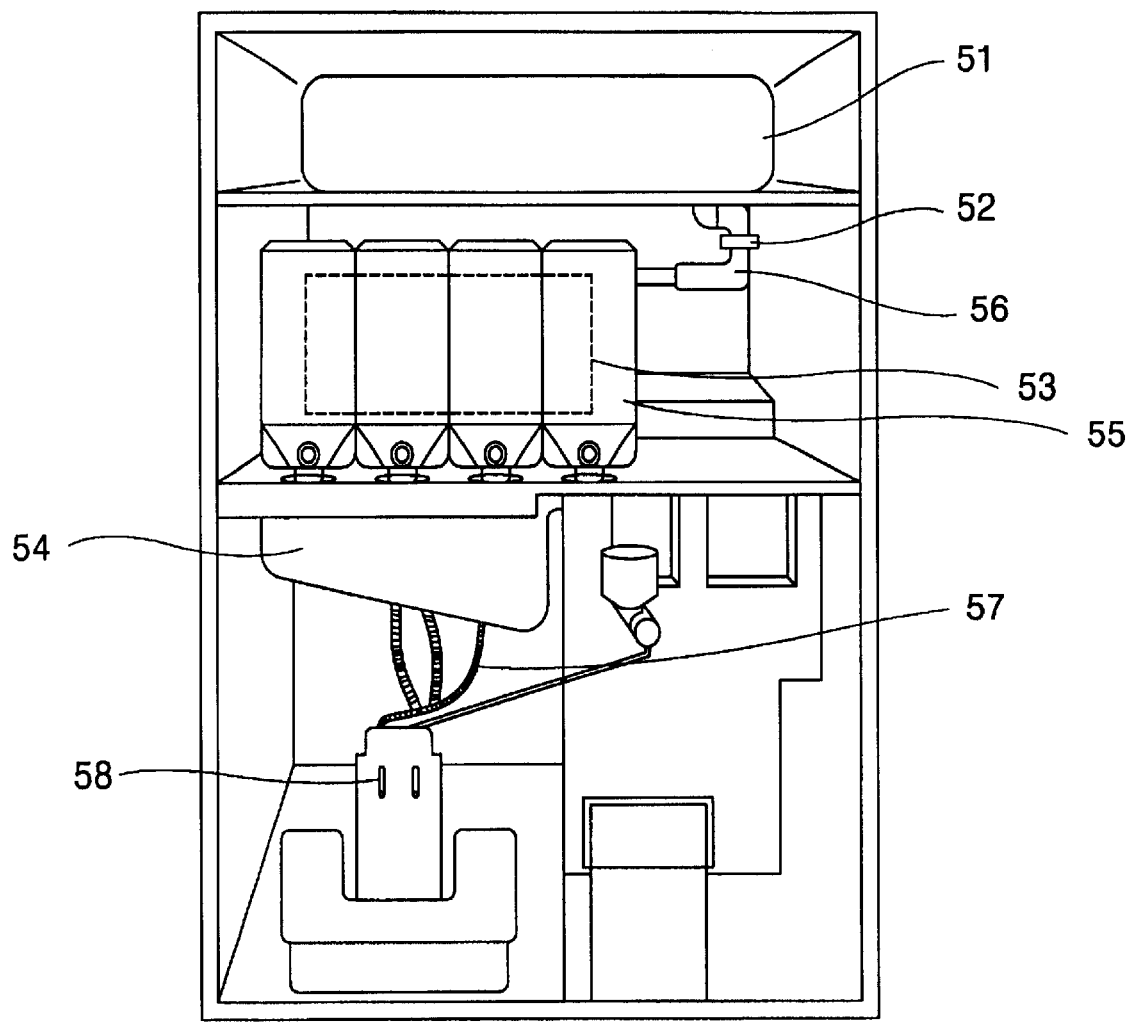
FIG. 1 illustrates a conventional automatic vending machine in which drinking water supplied from a water tank is sterilized by a UV lamp.
Figure 2A:
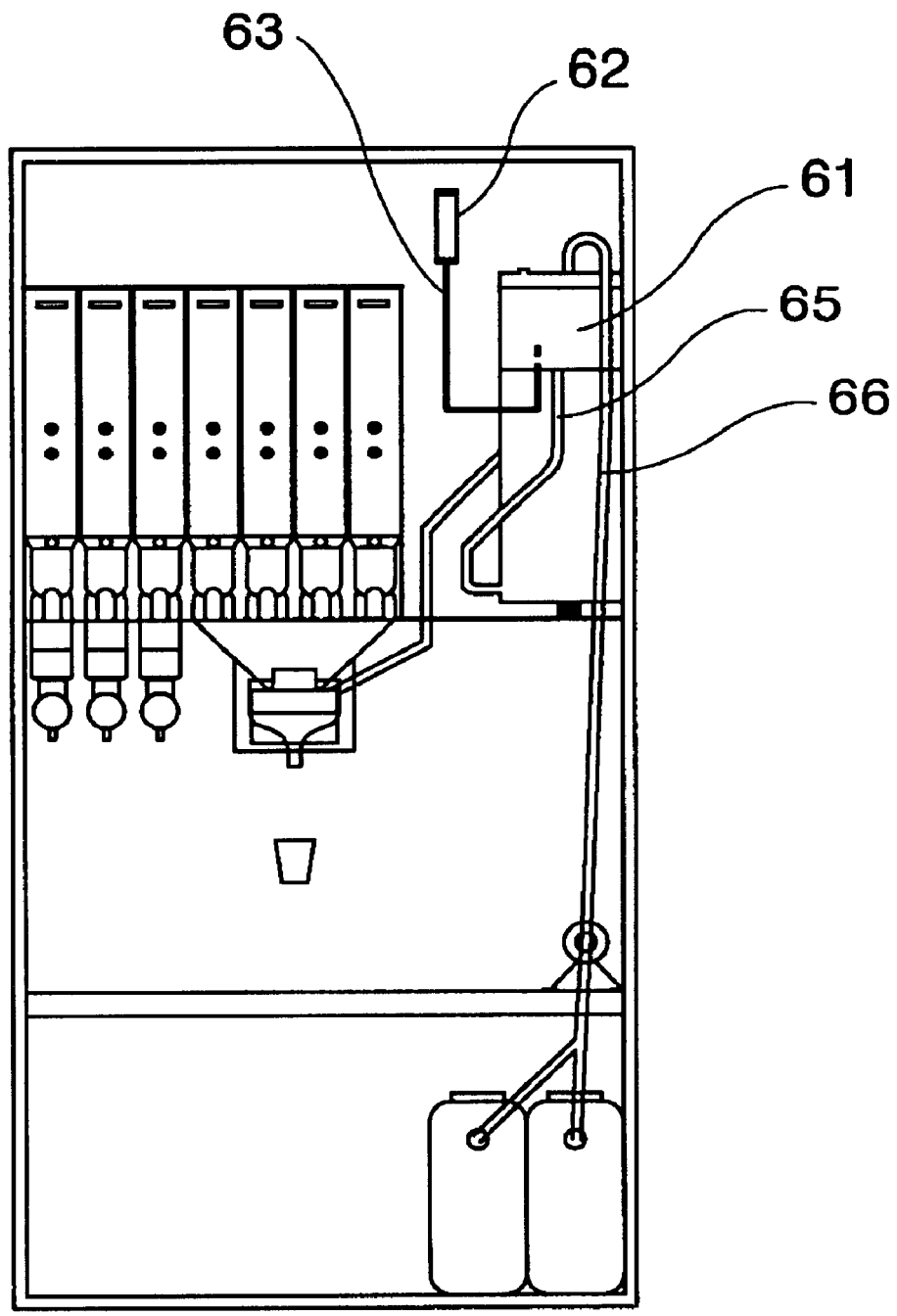
FIG. 2 illustrates another conventional automatic vending machine in which water contained in a water tank is sterilized by ozone generated in air by an ozone generator.
Figure 2B:
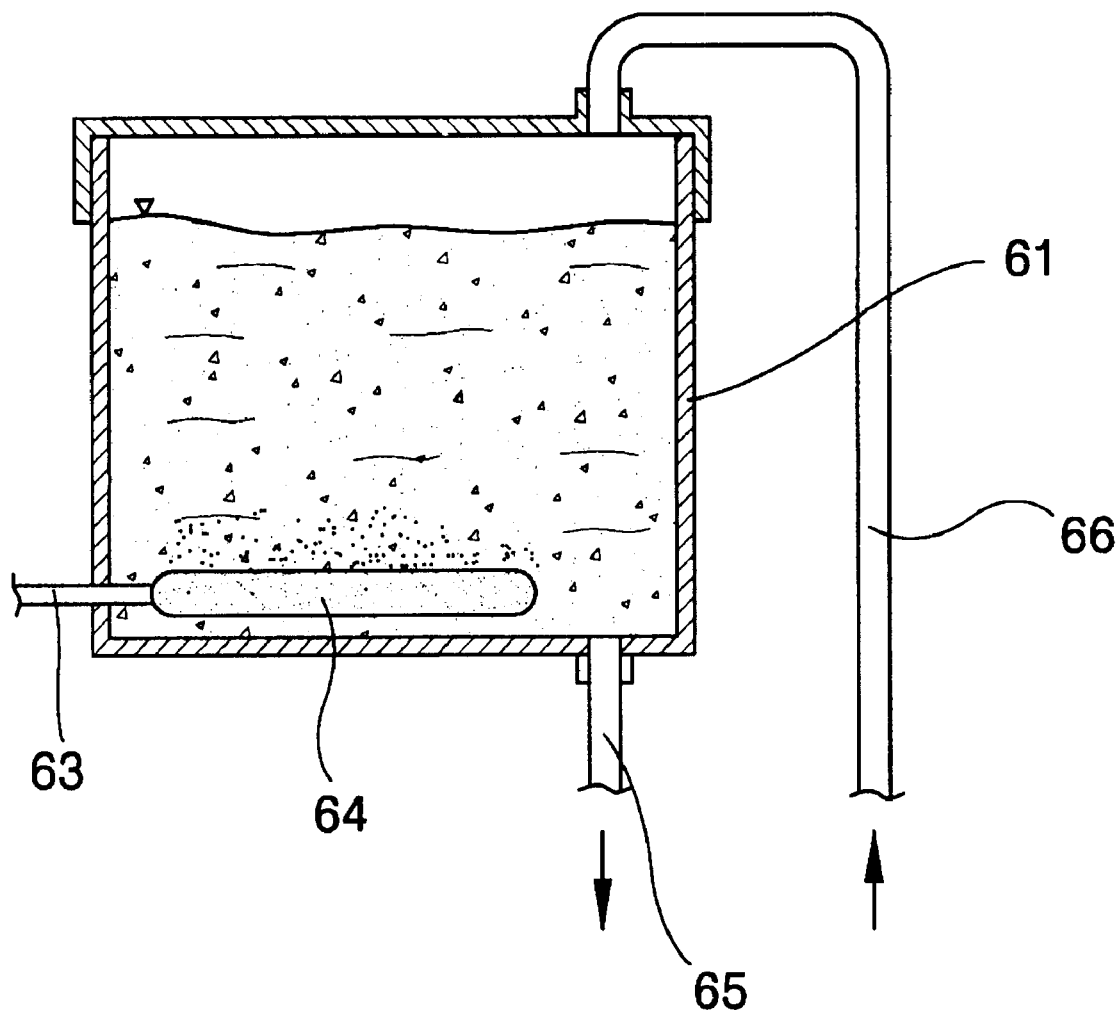

Prior to detailed description of the structure of an automatic vending machine according to the present invention, the structure and operation of a conventional automatic vending machine will first be described. As shown in FIG. 1, the conventional automatic vending machine includes a water supply tank 51 for supplying drinking water, a hot water tank 53 connected to the water supply tank 51 by means of a guide duct, for heating the water supplied from the water supply tank 51, and a discharge duct through which heated water flows from the hot water tank 53. Also, a water supply duct for supplying water is installed under the water supply tank 51. The water supply duct has a water supply valve installed to control the supply of water to the hot water tank 53. Also, a plurality of ingredient storage tanks 55, in which beverage ingredients such as coffee powder, sugar or the like, are stored, are installed in front of the hot water tank 53. Each of the storage tanks 55 has a discharge motor for discharging an ingredient contained therein. A mixing tub 54 for mixing the ingredients is installed under the storage tanks 55. An outlet duct 57 connected to the outside is installed under the mixing tub 54.

The operation of the conventional automatic vending machine will now be described. First, if an operation signal is input by external manipulation, drinking water from the water supply duct is supplied to the hot water tank 53 by the opening of the water supply valve, and the water supplied to the hot water tank 53 is heated and then introduced to the mixing tub 54 through the discharge duct. At the same time with the supply of water, the discharge motor starts to operate so that the ingredients in the storage tanks 55 are discharged to the mixing tub 54. In the mixing tub 54, the ingredients and water are mixed and the mixed beverage is discharged through the outlet duct 54 by means of a water supply cock 58 to be finally taken by a user.

Figure 3:
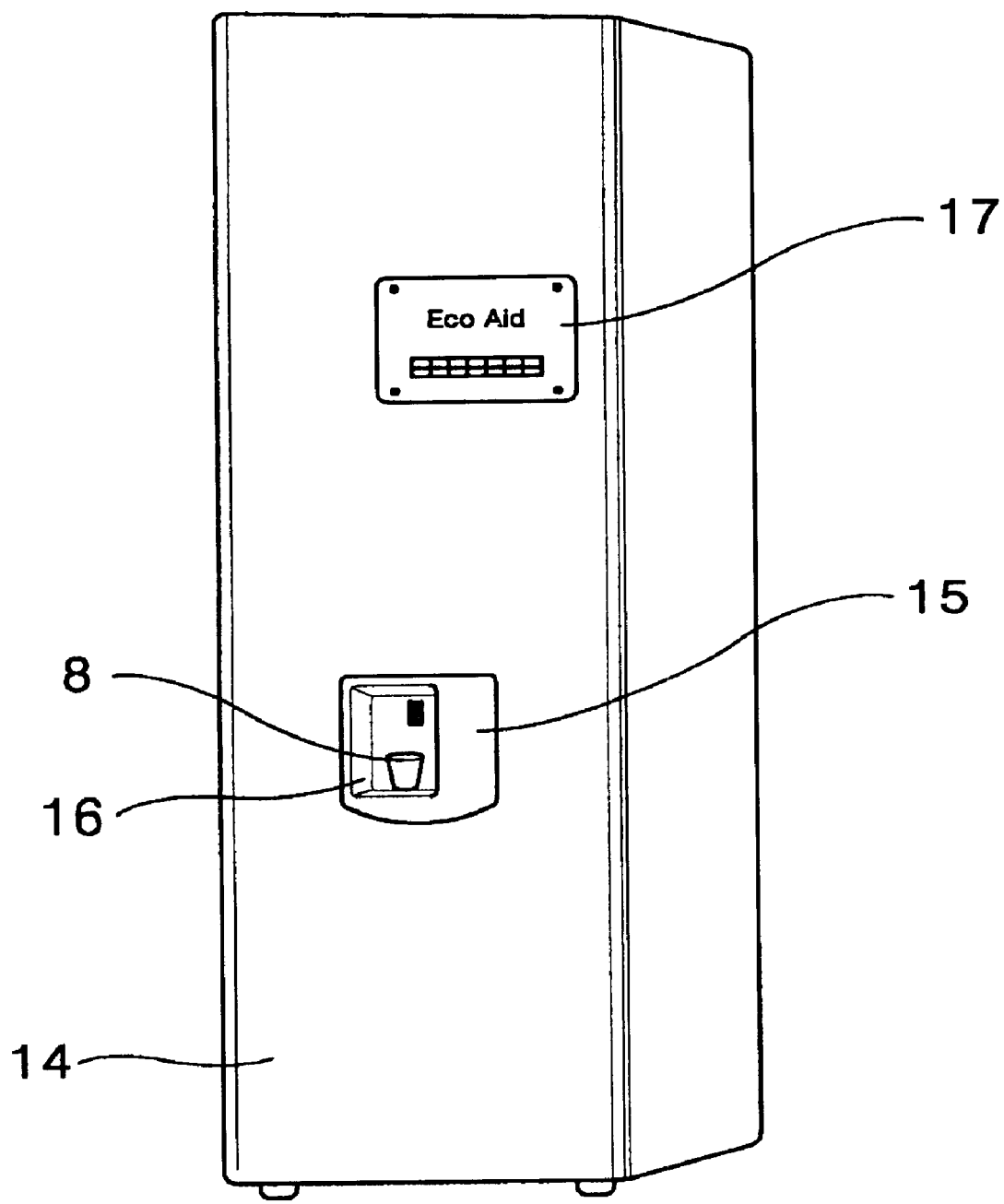
FIG. 3 is an external perspective view of an automatic vending machine with a functional water generator according to an embodiment of the present invention.

Compared with the structure of the aforementioned conventional automatic vending machine, the structure and operation of the automatic vending machine according to the present invention will now be described. FIG. 3 is an external perspective view of an automatic vending machine with a functional water generator according to an embodiment of the present invention, FIG. 4 is a schematic perspective view illustrating the internal structure thereof, and FIG. 5 schematically illustrates the operation mechanism thereof.

Referring to FIG. 3, the automatic vending machine according to an embodiment of the present invention, like conventional one, has a door 14 hinged on the front of the housing 13. and is provided with a coin slot and key input part 17, a distribution rack 15 where a beverage is poured into a cup 8, and an opening portion 16 configured to take out the beverage.

Figure 4:
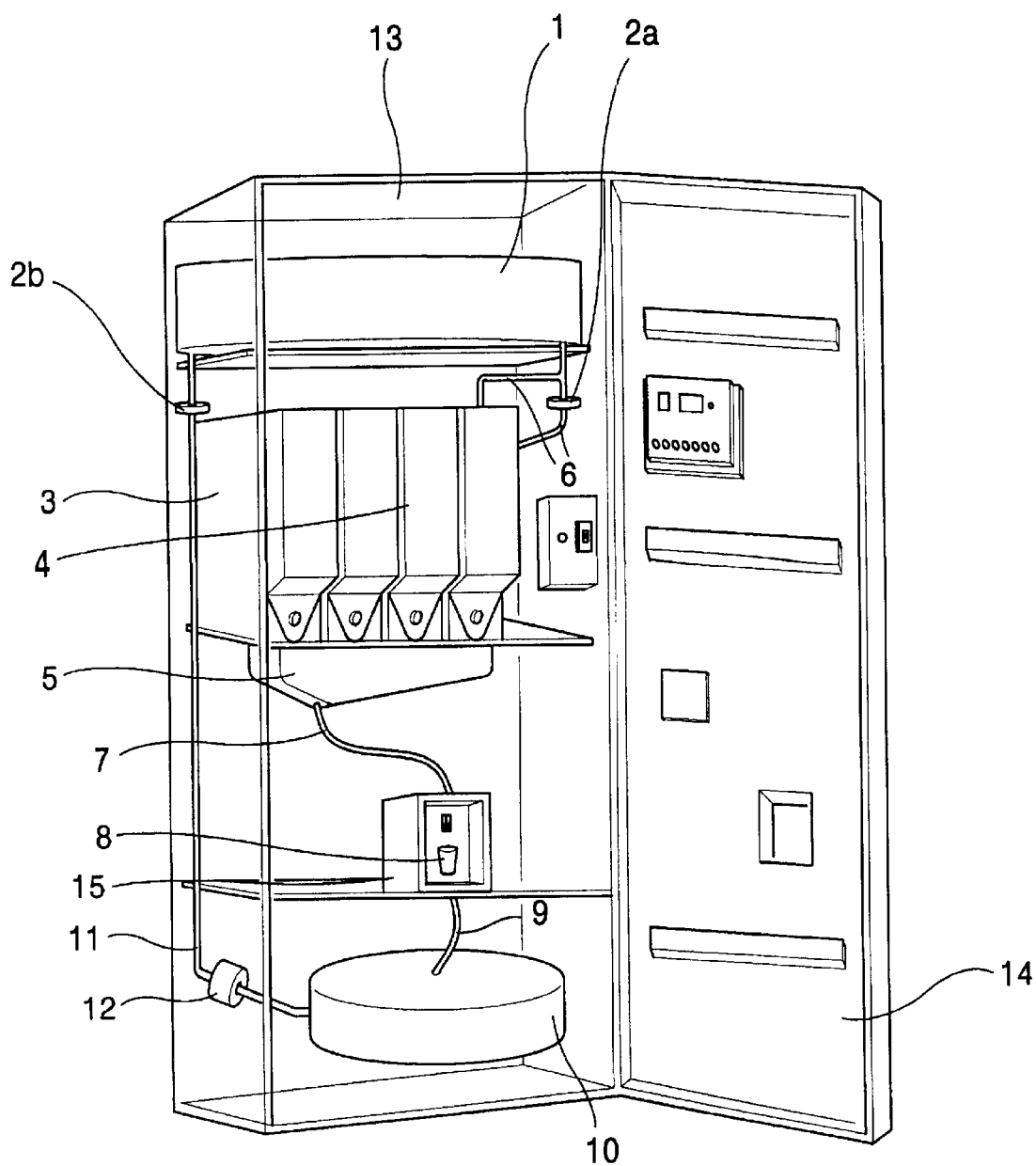
FIG. 4 is a schematic perspective view illustrating the internal structure of the automatic vending machine with a functional water generator according to an embodiment of the present invention.

Referring to FIG. 4 showing the internal structure of the housing 13, a water tank 1 in which drinking water is stored, and ingredient containers 4 in which beverage ingredients are stored, are installed in the upper part of the housing 13. Also, a water supply duct 6 for supplying water from the water tank 1 is connected to the water tank 1. In the automatic vending machine according to the present invention, the water tank 1 and the water supply duct 6 constitute a water supplier. Alternatively, the water supply duct 6 may be directly connected to a faucet, instead of the water tank 1. In this embodiment, the water supply duct 6 has two paths: one is connected to a cold/hot water tank 3 for cooling/heating the water supplied from the water tank 1; and the other is connected to a functional water generator 2. The two-paths water supply duct 6 is connected to a mixing tub 5 in which the water and beverage ingredients are mixed, through the opening of the valves. A discharge duct 7 for discharging the mixed beverage is formed under the mixing tub 5. The discharge duct 7 is configured to open above the cup 8 in the distribution rack 15. A collecting duct 9 for collecting liquid leaked outside when the mixed beverage is poured into the cup 8 from the discharge duct 7, and a water-collecting vessel 10, are provided under the distribution rack 15. A recycling duct 11 is connected to the water tank 1 from the collecting vessel 10. A purifying filter 12 for purifying the leaked liquid is mounted along the reccycling duct 11. Separately from the functional water generator 2a installed along the water supply duct 6, another functional water generator 2b is further installed along the recycling duct 11 in the vicinity of the water tank 1.

Figure 5:
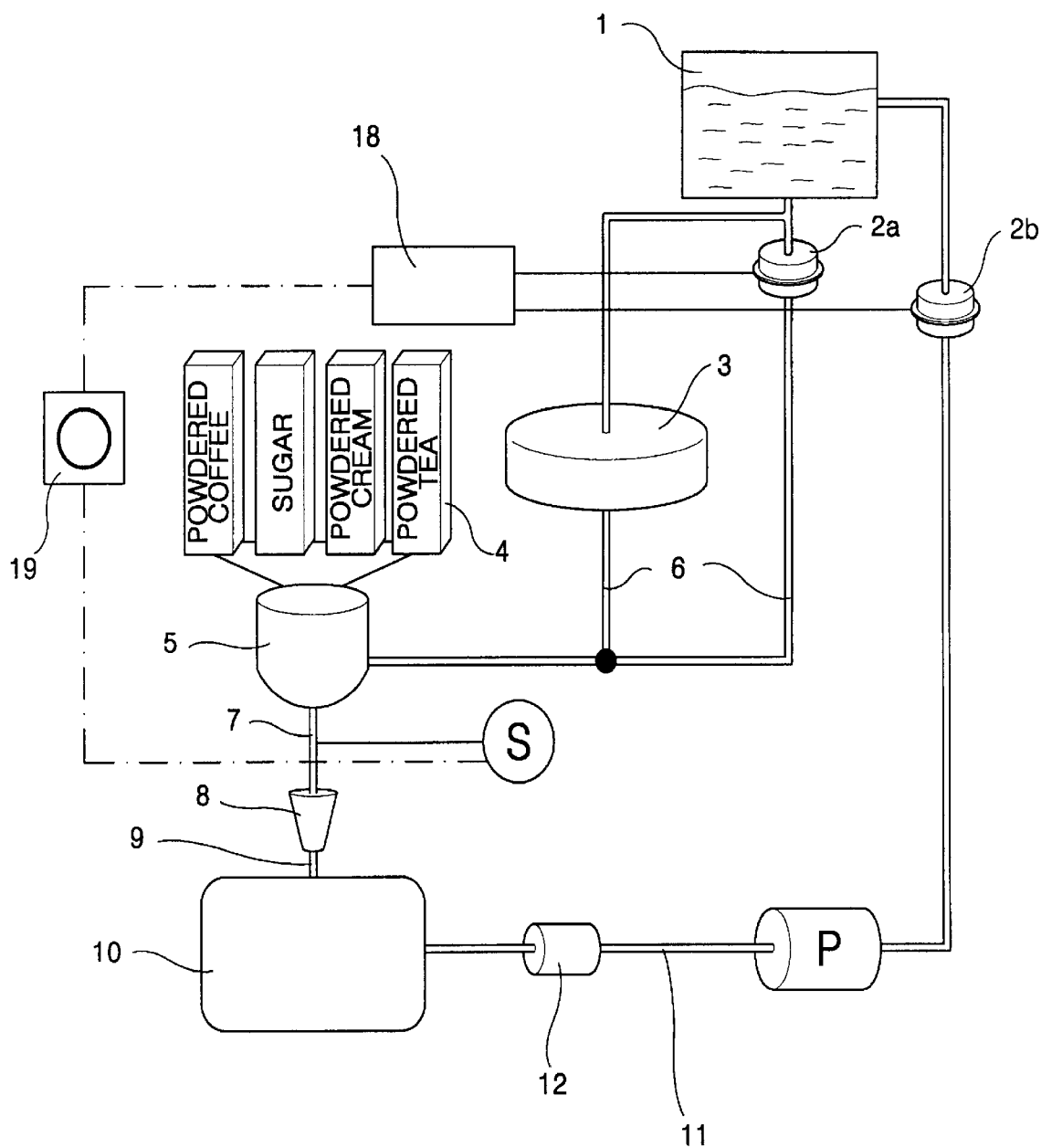
FIG. 5 schematically illustrates the operation mechanism of the automatic vending machine with a functional water generator according to an embodiment of the present invention.

Referring to FIG. 5, a power source 18 for applying voltage is connected to the functional water generators 2a and 2b installed in the water supply duct 6 and the recycling duct 11, respectively. The operation of the power source 18 is controlled by a controller 19. Also, a sensor S is installed on the water supply duct 6 or the discharge duct 7 for the purpose of sensing the concentration of the functional water flowing in the ducts when the functional water generators 2a and 2b operate. The controller 19 controls the operation of the power source 18 connected to the functional water generators 2a and 2b in accordance with a signal from the sensor S.

Next, the operation of the automatic vending machine with a functional water generator according to the present invention will be described. Like the conventional automatic vending machine, when a user puts a coin into a coin slot installed in the automatic vending machine and selects one kind of beverage through the key input part 17, the automatic vending machine is put into operation. First, the controller 19 selects the beverage ingredients for the selected beverage to be discharged from the ingredient containers 4 into the mixing tub 5 by predetermined amounts. Simultaneously, the valve of the water supply duct 6 opens, and then cold water or hot water is selected to be discharged into the mixing tub 5, thereby mixing the ingredients and the selected water to prepare the desired beverage. Then, the cup 8 stored in a cup dispenser is carried to the distribution rack 15 and the beverage mixed in the mixing tub 5 is discharged by a predetermined amount to the cup 8 through the discharge duct 7 which is operated by a discharge motor. After discharging the leverage, the user takes out the beverage-containing cup 8 through the opening portion 16. The liquid, which is discharged from the discharge duct 7 but is poured outside the cup 8, is collected in the water-collecting vessel 10 through the collecting duct 9 and then recycled into the water tank 1 through the recycling duct 11. The above-described operation is a beverage purchasing procedure generally conducted by a user.

If a voltage is applied to the power source, 18 the functional water generator 2a mounted on the water supply duct 6 starts to operate so that the water in the water supply duct 6, supplied from the water tank 1, is electrolyzed to generate functional water. The functional water in the water supply duct 6 sterilizes, disinfects, deodorizes and washes the conduits and containers installed inside the automatic vending machine while passing through the mixing tub 5 and the discharge duct 7. Also, while the functional water discharged outside through the discharge duct 7 is recycled into the water tank 1 via the collecting duct 9, the water-collecting vessel 10, the purifying filter 12 and the recycling duct 11, it sterilizes, disinfects, deodorizes and washes the conduits and containers installed inside the automatic vending machine. The functional water recycled into the water tank 1 keeps flowing through the water supply duct 6 having the cold/hot water tank 3 and is discharged outside via the cold/hot water tank 3, the mixing tub 5 and the discharge duct 7, to sterilize, disinfect, deodorize and wash the overall conduits and containers of the automatic vending machine.

The functional water generator 2b mounted on the recycling duct 11 starts to operate by the controller 19 and converts water in the recycling duct 11 into functional water. The functional water generated in the recycling duct 11 is recycled into the water tank 1 and then sterilizes, disinfects, deodorizes and washes the inside of the water tank 1 and the water stored therein. Thereafter, the functional water is discharged outside through the water supply duct 6, the mixing tub 5 and the discharge duct 7 or recycled along the recycling duct 11.

The operations of the functional water generator 2a or 2b are controlled by the concentration of the functional water in the water supply duct 6 or the discharge duct 7. When the concentration of the functional water reaches a constant level, the sensor S mounted on the discharge duct 7 senses it and the functional water generator 2a or 2b stop operating in accordance with the signal from the controller 19.

The functional water generated from the functional water generators 2a or 2b includes concentrated ozone or cations or anions, and therefore sterilizes, disinfects, deodorizes and washes the inside of the machine and drinking water and then normally be discharged outside through the discharge duct 7. In case of ozone water containing a large quantity of oxygen molecules, the flavor of water is enhanced as the amount of dissolved oxygen increases, thereby improving the flavor of a beverage. Eventually, the automatic vending machine according to the present invention may provide a sterilized oxygen-rich beverage.

Figure 6:
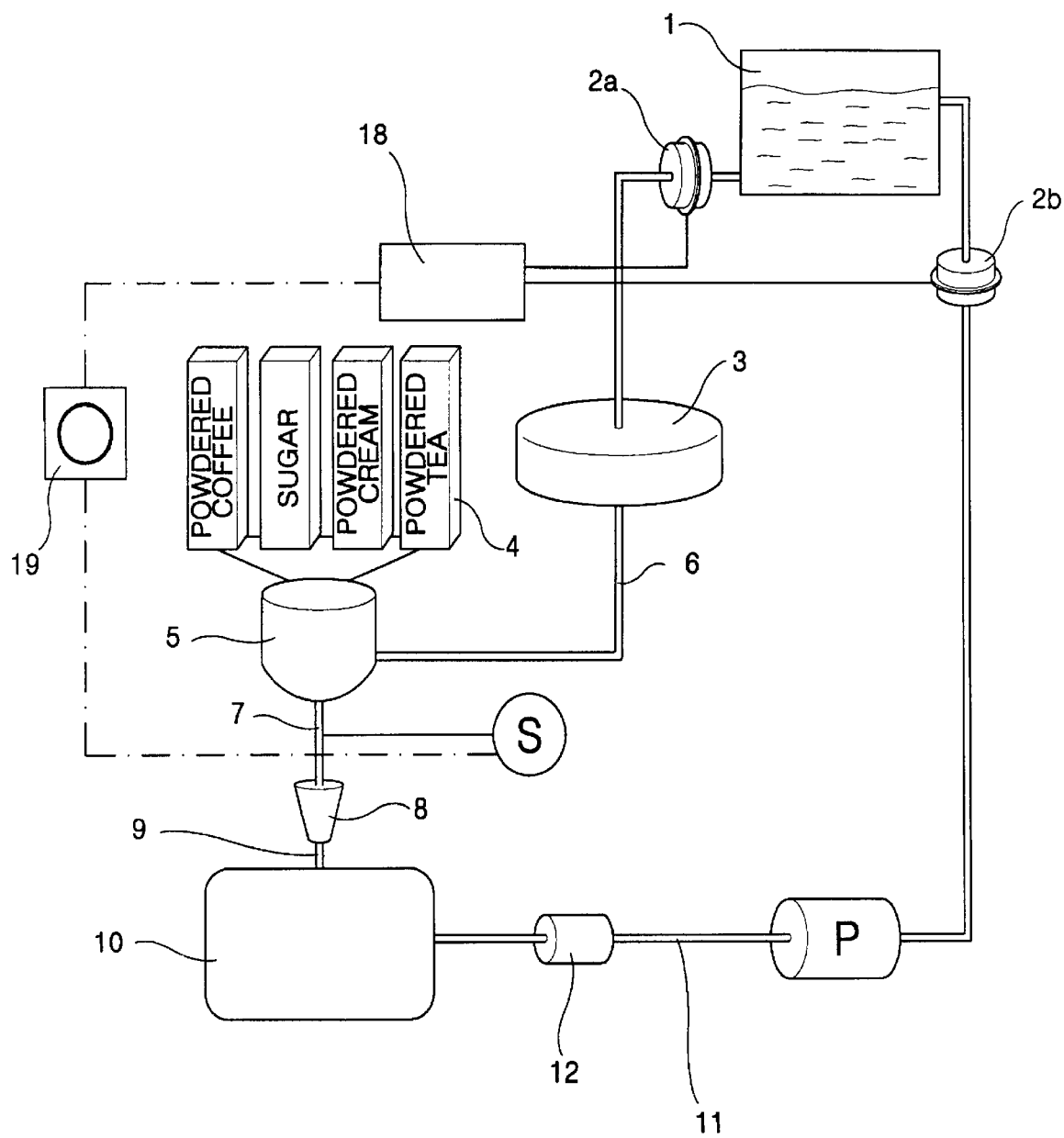
FIG. 6 schematically illustrates the operation mechanism of the automatic vending machine with a functional water generator according to another embodiment of the present invention.

FIG. 6 schematically illustrates the operation mechanism of an automatic vending machine with a functional water generator according to another embodiment of the present invention. In the embodiment shown in FIG. 5, the water supply duct 6 has two paths so that one is connected to the cold/hot water tank 3 and the other is connected to the functional water generator 2a, respectively. On the other hand, according to this embodiment, the water supply duct 6 has one path that is sequentially connected to the functional water generator 2 and the cold/hot water tank 3. With the exception of the fact described above, the structure and operating mechanism of the automatic vending machine according to this embodiment is the same as those of the automatic vending machine shown in FIG. 5 in every respect.

Figure 7:
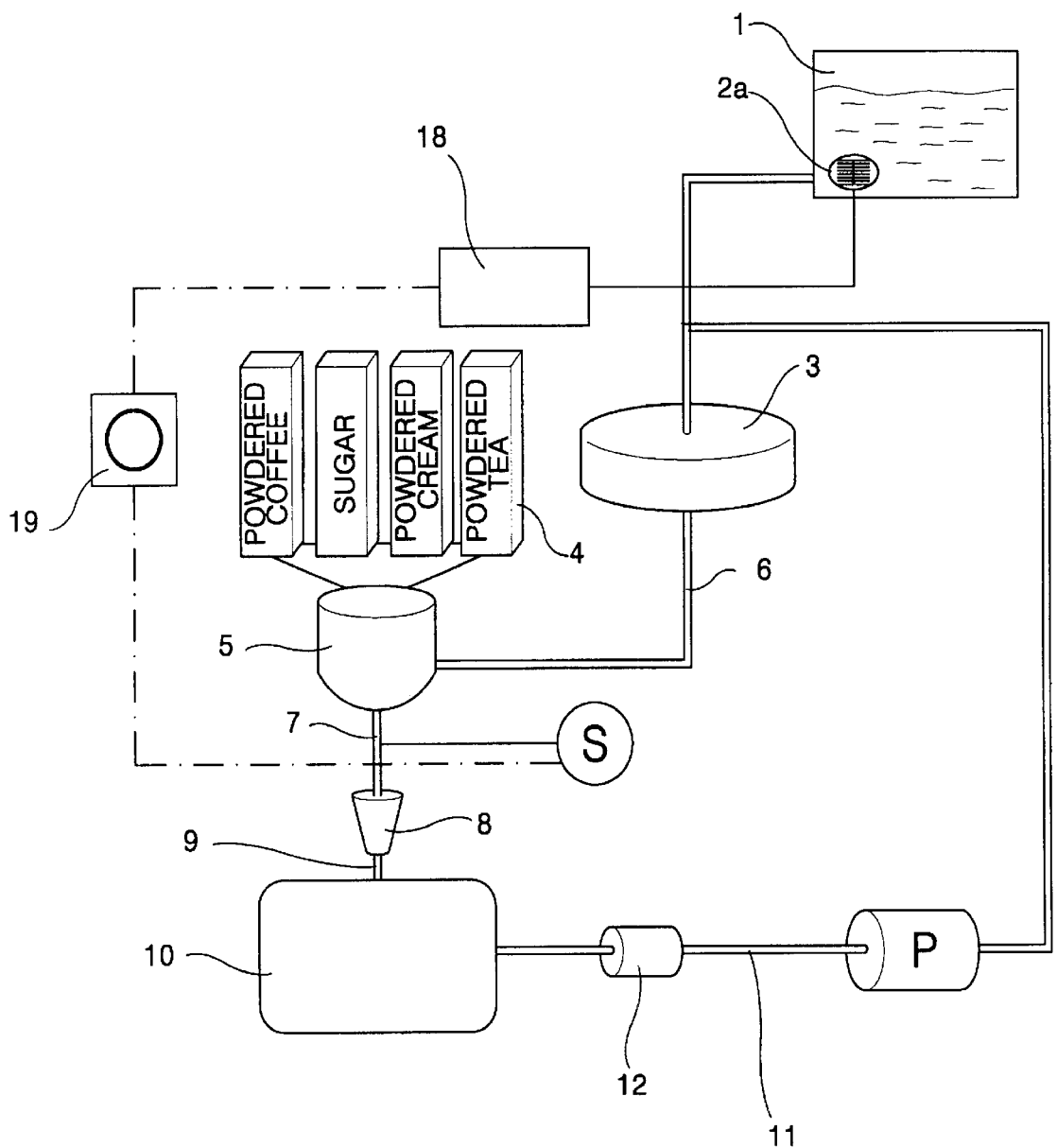
FIG. 7 schematically illustrates the operation mechanism of the automatic vending machine with a functional water generator according to still another embodiment of the present invention.
Figure 8:
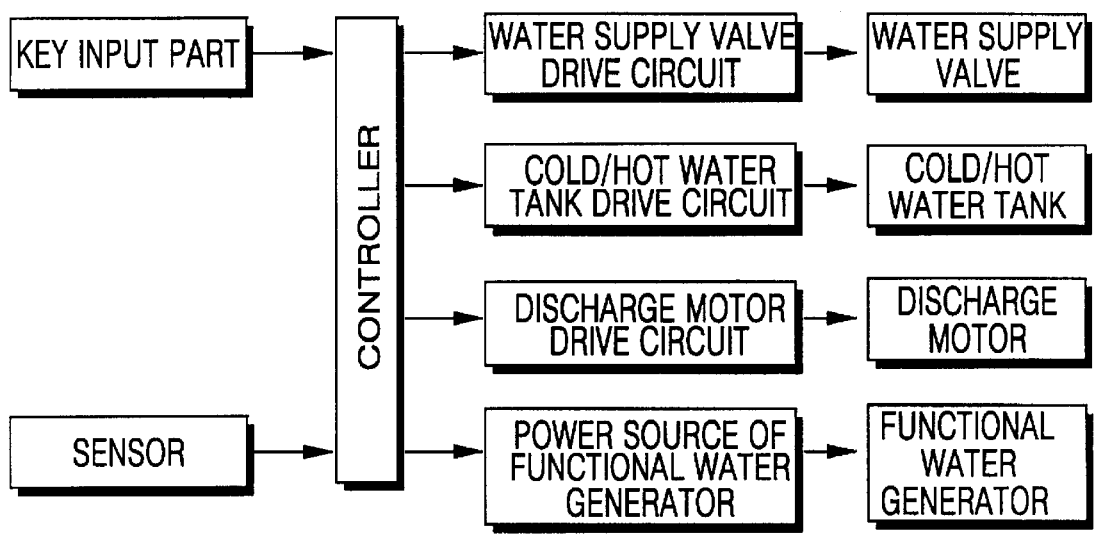
FIG. 8 is a control block diagram showing the operation of the automatic vending machine with a functional water generator according to the present invention.

FIG. 7 schematically illustrates the operation mechanism of the automatic vending machine with a functional water generator according to still another embodiment of the present invention. This embodiment is different from the embodiment shown in FIG. 5 in that a functional water generator 2a is provided inside a water tank 1, a recycling duct 11 is directly connected to a water supply duct 6, not to the water tank 1, and a functional water generator 2b is not separately installed. In this case, if a voltage is applied to a power source 8 of the functional water generator 2a by a controller 19, the operation of the functional water generator 2a mounted in the water tank 1 is initiated so that the water in the water tank 1 is electrolyzed to generate functional water. While the generated functional water passes through the water supply duct 6, a mixing tub 5, a discharge duct 7, a collecting duct 9, a water-collecting vessel 10, a purifying filter 12 and the recycling duct 11 until it is recycled into the water tank 1, the functional water sterilizes, disinfects, deodorizes and washes various conduits and containers. FIG. 8 is a control block diagram showing the operation of the automatic vending machine with a functional water generator according to the present invention.

A functional water generator mounted in the automatic vending machine according to the present invention will now be described in detail. In the present invention, the functional water may be either ozone water or electrolyzed water. Thus, the functional water generator may include an ozone water generator and an electrolyzed water generator.

Figure 9A:
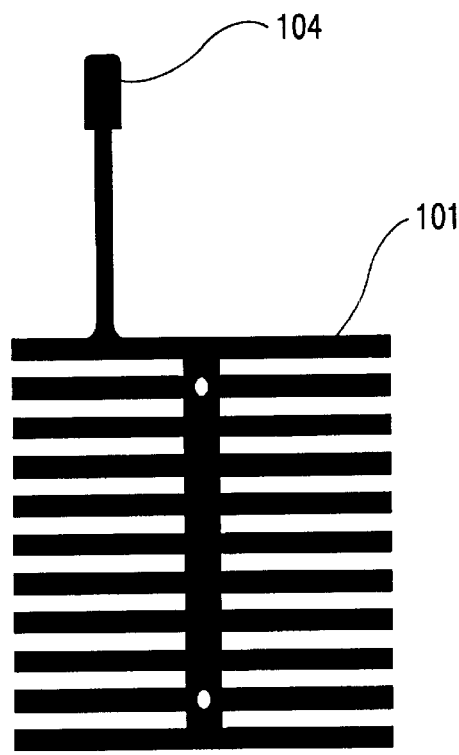
Figure 9B:
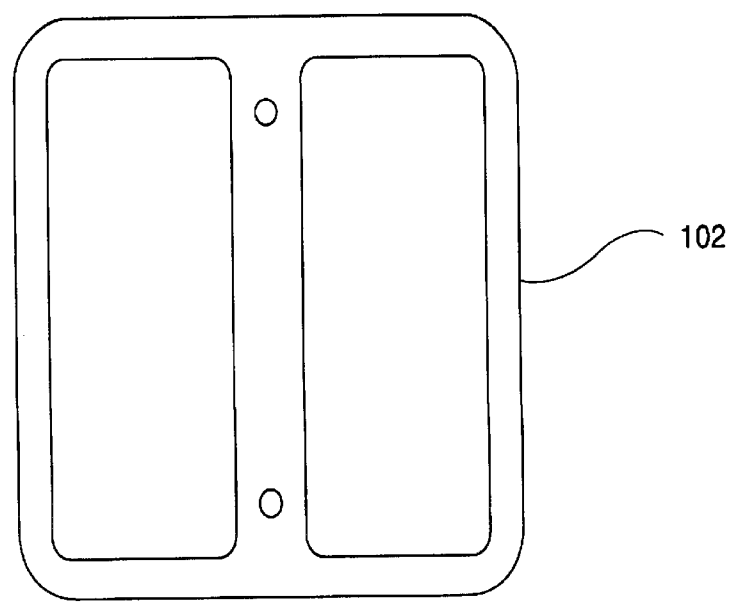
Figure 9C:
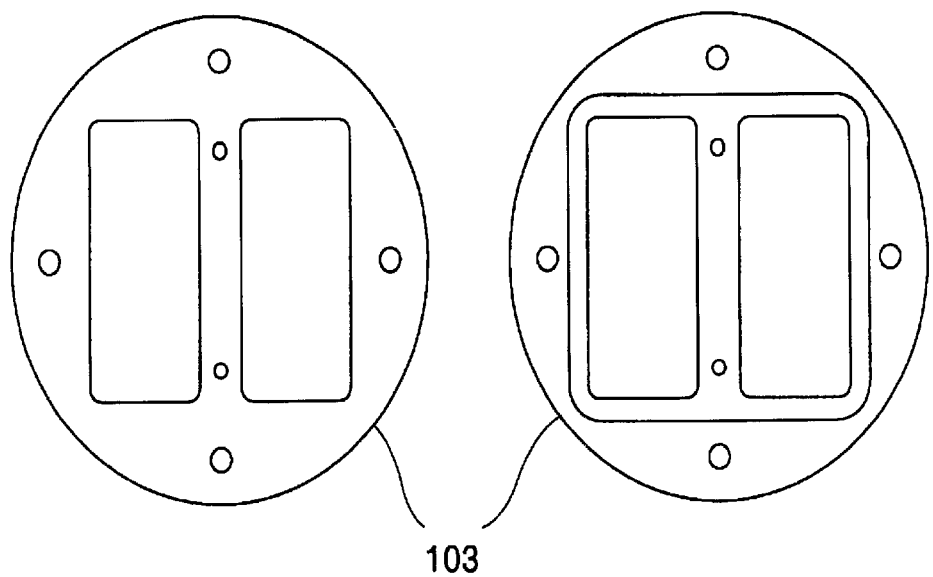
Figure 9D:
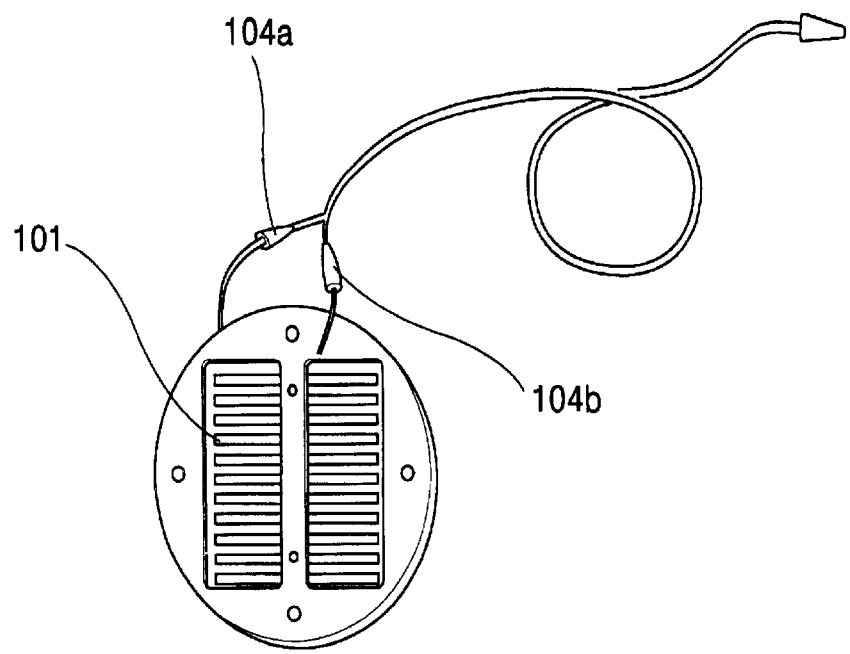

First, the ozone water generator includes at least one pair of facing electrodes. FIGS. 9A through 9D and FIG. 10 illustrate examples of an ozone water generator that can be used for an automatic vending machine according to the present invention. FIG. 9A shows one of a pair of facing electrodes 101a and 101b, of a fish bone type, FIG. 9B shows a spacer 102 for maintaining a gap between a pair of facing electrodes, FIG. 9C shows an electrode fixing frame 103, and FIG. 9D shows an ozone water generator fixed on a frame, in which a pair of facing electrodes is vertically disposed with a spacer interposed therebetween. The ozone water generator shown in FIGS. 9A through 9D is generally called a bare type or nude type ozone water generator having bare electrodes, and is directly put into water as used. External electrode connection terminals 104a and 104b are provided at one side of each of the facing electrodes 101a and 101b, respectively. When a voltage is applied to the external electrode connection terminals 104a and 104b, water molecules are decomposed between the facing electrodes 101a and 101b to generate ozone, thereby generating ozone water. The bare type ozone water generator is not required to be fixed in water and can be preferably used when control of water flow is not required. Thus, in the automatic vending machine according to the present invention, the ozone water generator of bare type is desirably used in the embodiment shown in FIG. 7 in which the functional water generator is provided in the water tank.

Figure 10:
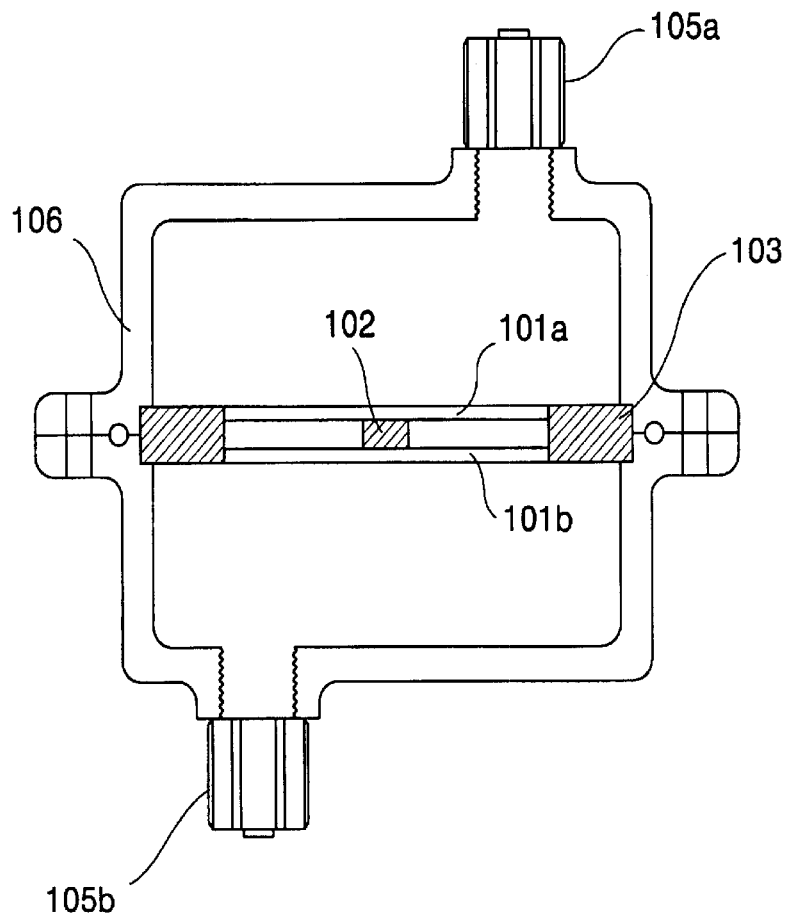
FIG. 10 is a cross-sectional view showing another example of an ozone water generator for use in the automatic vending machine according to the present invention.

FIG. 10 is a cross-sectional view showing another example of an ozone water generator for use in the automatic vending machine according to the present invention. The ozone water generator includes a pair of facing electrodes 101a and 101b vertically disposed with a spacer 102 interposed therebetween and then fixed to a frame 103. The ozone water generator, mounted inside a container 106 having water inlet and outlet 105a and 105b, is generally called a cell type ozone water generator. Since the ozone water generator of cell type has water inlet and outlet, it may be fixed to the wall or bottom and be preferably used when control of water flow is required. In the automatic vending machine of the present invention, the ozone water generator of cell type is desirably used in the embodiments shown in FIGS. 5 and 6 in which the functional water generator is inserted into a water supply duct or a recycling duct.

The electrolyzed water generator that may be used for an automatic vending machine according to the present invention is constructed such that a positive electrode and a negative electrode face to each other with a separating layer disposed therebetween in a case having a water supply duct and an electrolyzed water drain duct. During passed from the water supply duct through the facing electrodes, water is electrolyzed by a voltage applied to the electrodes to generate acid water and alkali water, which is drained through the drain duct. In the electrolyzed water generator, the positive electrode water output from the drain duct of the positive electrode is acid water containing strongly acidic materials, for example, a large amount of $O_3$ and trace amounts of $O_2$, $O$ and $H_2O_2$, that is, containing many anions. The negative electrode water output from the drain duct of the negative electrode is alkali water containing many cations. The amount and ion concentration of the strongly acidic materials such as $O_3$, $O_2$, $O$, $H_2O_2$ or the like, can be easily adjusted by controlling the magnitude or cycle of the voltage applied manually or automatically, for example, by using an automatic control circuit. Also, the amount and ion concentration of the strongly acidic materials can be adjusted by varying the sizes of electrodes, the distance between electrodes, the width or amount of water flow. Further, weak alkali water and weak acid water as well as neutral water of pH 7 can be made by using a means for mixing and neutralizing the positive electrode water (strong acid water) and the negative electrode water (strong alkali water) output through the drain ducts of the respective electrodes. Such neutral water contains a considerable amount of oxidizing materials generated by discharge and electrolysis, therefore, has a sufficient sterilizing and disinfecting effect. Thus, the neutral water can also be advantageously used for the purpose of sterilization and disinfection.

In case the electrolyzed water generator is installed in the automatic vending machine according to the present invention, acid water, alkali water or neutral water can be selectively prepared based on the option by a controller. Thus, the electrolyzed water of an appropriate type can be generated for use according to the purpose of sterilization, disinfection, deodorization or washing of the inside of the automatic vending machine. For example, after circulating acid water inside the machine, drinkable weak alkali water is generated and circulated, thereby neutralizing the previous trace of acid water. Also, after circulating acid water or alkali water, neutral water is preferably circulated.

In the above-described ozone water generator or electrolyzed water generator, the facing electrodes are preferably made of platinum (Pt), a platinum/palladium (Pt/Pd) alloy, a Pt group/Pd alloy, or a conductive metal such as titanium (Ti) coated with Pt, a Pt/Pd alloy or a Pt group/Pd alloy. In case of using the Pt/Pd alloy, 85.0 to 99.95 wt % of Pt and 15.0 to 0.05 wt % of Pd are preferably contained in the alloy. Carbon electrodes having electric conductivity and other electrode properties manufactured by subjecting carbon powder extracted from charcoal or carbon fiber obtained by carbonizing polyacryl fibers to a compressive molding process at high-temperature and high-pressure condition and a high-temperature carbonization process, can also be used for the facing electrodes of the functional water generator according to the present invention. When the carbon electrodes are employed to the functional water generator according to the present invention, they exhibit similar properties and performance to metallic conductors and are cost-efficient.

Also, the distance between the facing electrodes of the functional water generator is preferably 0.1 to 1 mm, and the structure thereof may be a panel type, a flat panel type having one or more holes, a small strip type, a fine wire type, a fish bone type, a mesh type or a cylinder type. Although square electrodes have been illustrated and described in the embodiment, the facing electrodes may have any shapes, including a circular or rectangular shape.

In the ozone water generator or electrolyzed water generator according to the present invention, a direct-current (DC) voltage, a pulse voltage, a square wave pulse voltage, a sequence-controlled pulse voltage or an alternating pulse voltage can be applied to the facing electrodes.

Figure 11:
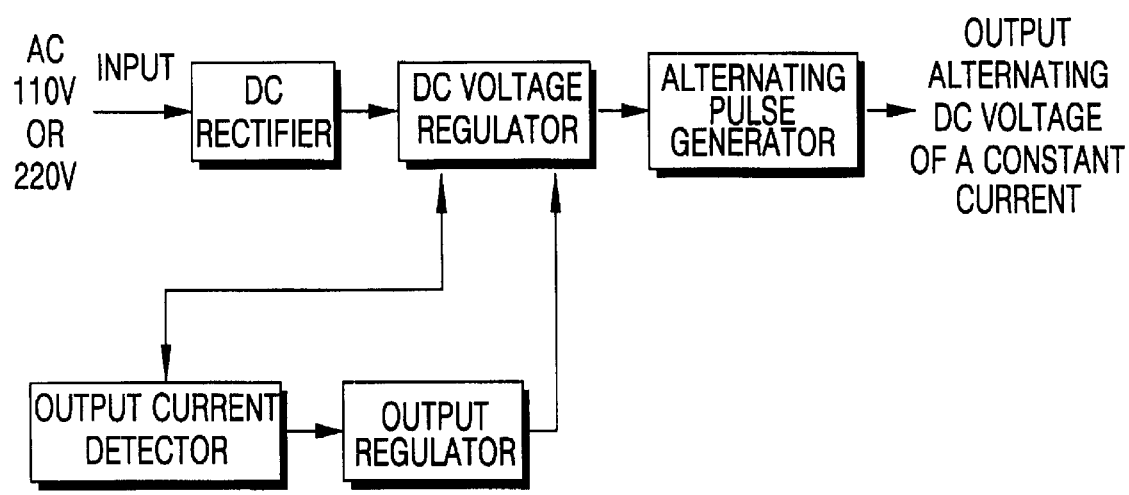
FIG. 11 is a block diagram of a power generation mechanism applied to the functional water generator which can be used in the automatic vending machine according to the present invention.

FIG. 11 is a block diagram of a power generation mechanism applied to the functional water generator which can be used in the automatic vending machine according to the present invention. Here, an AC voltage of 110 or 220 V is applied to a DC rectifier for DC rectification to generate a predetermined DC voltage. Next, the DC voltage regulator detects output current and regulates output current into a constant magnitude to prevent the DC voltage from varying due to the change of the AC voltage of 110 or 220 V. The adjusted DC voltage is output as an alternating DC voltage of a constant current via an alternating pulse generator.

The following examples are provided for showing the sterilizing efficiency of the automatic vending machine having the functional water generator according to the present invention.

EXAMPLE 1

Sterilizing Efficiency

An ozone water generator shown in FIG. 10 was mounted on a water supply duct of the automatic vending machine shown in FIG. 5, and the sterilizing efficiency was tested while adjusting currents. The water tank of the machine was filled with tap water containing bacteria (*E coli* and O-157) in a concentration of 1,400 cells/ml, and then the ozone water generator was operated. Then, the number of bacteria contained in the discharged water was examined according to the lapse of time.

Table 1 shows the number of bacteria according to the operation of the ozone water generator installed in the automatic vending machine according to the present invention.

TABLE 1

| Current (A) | | 1 | 2 |
|---|---|---|---|
| Voltage (V) | | 40 | 60 |
| Ozone concentration (ppm) | | 0.3 | 0.3 |
| Number of bacteria | Raw water | 140 | 140 |
| (CFU/0.1 ml) | After 10 sec | 0 | 0 |
| | After 30 sec | 0 | 0 |
| | After 60 sec | 0 | 0 |

As confirmed from Table 1, the bacteria contained in drinking water were completely sterilized within 10 seconds by the ozone water generator mounted in the automatic vending machine according to the present invention.

EXAMPLE 2

Sterilizing Efficiency

An ozone water generator shown in FIG. 9 was mounted on a water tank of the automatic vending machine shown in FIG. 7, and the sterilizing efficiency was tested. The water tank of the machine was filled with tap water containing *E coli* and O-157 in concentrations of $2.5 \times 10^3$ cells/ml and $1.5 \times 10^3$ cells/ml, respectively, and then the ozone water generator was operated. Then, the number of bacteria contained in the discharged water was examined according to the lapse of time. The voltage applied to the ozone water generator was 1 A and 1 V, and the ozone concentration was 0.3 ppm.

Table 2 shows the number of bacteria according to the operation of the ozone water generator installed in the automatic vending machine according to the present invention.

TABLE 2

| Current (A) | | 1 | 1 |
|---|---|---|---|
| Ozone concentration (ppm) | | 0.3 | 0.3 |
| Number of bacteria | Raw water | 250 | 150 |
| (CFU/0.1 ml) | After 10 sec | 18 | 0 |
| | After 30 sec | 0 | 0 |
| | After 60 sec | 0 | 0 |

As confirmed from Table 2, even when tap water was severely contaminated by bacteria, the automatic vending machine according to the present invention could sterilize over 90% of bacteria within 10 seconds.

As described above, in the automatic vending machine with a functional water generator according to the present invention, a functional water generator is installed in a water supplier of the automatic vending machine, that is, in a water tank or water supply duct, to generate functional water such as ozone water or electrolyzed water having various functions such as sterilization, disinfection, deodorization or washing, thereby simultaneously performing sterilization, disinfection, deodorization and washing of water as well as containers and conduits installed inside the machine, such as a water supply duct, a mixing tub, a water tank or the like. While the conventional automatic vending machine in which ozone gas is generated in air by the ozone generator and dissolved into the water stored in the water tank has the problems of safety and financial burden of equipment, in the automatic vending machine according to the present invention, sterilization, disinfection, deodorization or washing of both drinking water and containers and conduits in the machine can be simultaneously performed, without causing such problems as safety and cost.

What is claimed is:

1. An automatic vending machine comprising:
    a water supplier for supplying drinking water;
    a plurality of ingredient containers for storing beverage ingredients;
    a mixing tub for mixing the drinking water supplied from the water supplier and the beverage ingredients supplied from the ingredient containers;
    a discharge duct through which the mixed beverage is discharged;
    a functional water generator for generating functional water in the water supplier by facing electrodes provided to operate in water; and
    a power source for applying a direct-current (DC) voltage, a pulse voltage, a square wave pulse voltage, a sequence-controlled pulse voltage or an alternating pulse voltage to the functional water generator,
    wherein the functional water generator is an ozone water generator having at least one pair of facing electrodes or an electrolyzed water generator having at least one pair of facing electrodes disposed with a separating layer interposed therebetween.

2. The automatic vending machine according to claim 1, further comprising:
    a cold/hot water tank for cooling or heating the drinking water supplied from the water supplier; and
    a recycling duct for recycling a liquid leaked from the discharge duct into the water supplier.

3. The automatic vending machine according to claim 2, wherein the recycling duct includes a purifying filter and another functional water generator.

4. The automatic vending machine according to claim 1, wherein the facing electrodes are made of platinum (Pt), a platinum/palladium alloy (Pt/Pd) alloy or a Pt group/Pd alloy.

5. The automatic vending machine according to claim 1, wherein the facing electrodes are made of a conductive metal coated with Platinum (Pt), a platinum/palladium alloy (Pt/Pd) alloy or a Pt group/Pd alloy.

6. The automatic vending machine according to claim 5, wherein the conductive metal is titanium (Ti).

7. The automatic vending machine according to claim 1, wherein the facing electrodes are carbon electrodes have electric conductivity.

8. The automatic vending machine according to claim 1, wherein the facing electrodes are of a plane type, a flat panel type having one or more holes, a small strip type, a fine wire type, a fish bone type, a mesh type or a cylinder type, and the distance of the facing electrode is in the range of 0.1 to 1 mm.

9. The automatic vending machine according to claim 1, further comprising:
    a sensor for sensing the concentration of the functional water supplied via the functional water generator; and
    a controller for receiving information of the concentration of the functional water from the sensor and controlling the voltage to be applied to the power source.

10. An automatic vending machine comprising:
    means for supplying drinking water;
    means for supplying beverage ingredients;
    means for mixing the supplied drinking water with the beverage ingredients;

means for discharging the mixed beverage to the outside;

means for generating functional water in the drinking water by means of facing electrodes provided to operate in water; and means for applying a direct-current (DC) voltage, a pulse voltage, a square wave pulse voltage, a sequence-controlled pulse voltage or an alternating pulse voltage to the functional water generating means, wherein the functional water is ozone water or electrolyzed water.

11. The automatic vending machine according to claim 10, wherein the electrolyzed water is acid water, alkali water, or neutral water.

12. The automatic vending machine according to claim 10, further comprising:

means for cooling or heating the supplied drinking water; and means for recycling a liquid leaked from the discharging means to recycle into the drinking water.

13. The automatic vending machine according to claim 12, further comprising:

means for sensing the concentration of the functional water supplied via the functional water generating means; and means for controlling the generation of the functional water in accordance with the concentration of the functional water.

14. A washing method of an automatic vending machine comprising a water supplier for supplying drinking water, a plurality of ingredient containers for storing beverage ingredients, a mixing tub for mixing the drinking water supplied from the water supplier and the beverage ingredients supplied from the ingredient container, a discharge duct through which the mixed beverage is discharged, a functional water generator for generating ozone water or electrolyzed water in the water supplier by facing electrodes provided to operate in water, and a power source for applying a direct-current (DC) voltage, a pulse voltage, a square wave pulse voltage, a sequence-controlled pulse voltage or an alternating pulse voltage to the functional water generator, wherein the method comprises the steps of:

generating ozone water or electrolyzed water in the water supplier by applying a voltage to the functional water generator; and discharging the ozone water or electrolyzed water to the discharge duct through the mixing tub.

15. The washing method according to claim 14, further comprising the steps of:

recycling the discharged ozone water or electrolyzed water into the water supplier; and discharging the recycled ozone water or electrolyzed water to the discharge duct through the mixing tub.

16. The washing method according to claim 15, further comprising the steps of:

sensing the concentration of the supplied ozone water or electrolyzed water; and controlling the generation of the ozone water or electrolyzed water in accordance with the concentration of the drinking water.

17. The washing method according to claim 14, further comprising the steps of:

sensing the concentration of the supplied ozone water or electrolyzed water; and controlling the generation of the ozone water or electrolyzed water in accordance with the concentration of the drinking water.

* * * * *